United States Patent
Perez-Cruet et al.

(10) Patent No.: US 8,118,737 B2
(45) Date of Patent: Feb. 21, 2012

(54) RETRACTOR DEVICE FOR CERVICAL SPINAL FUSION

(75) Inventors: Miguelangelo J. Perez-Cruet, Bloomfield, MI (US); John A. Miller, Bloomfield Village, MI (US)

(73) Assignee: MI4Spine, LLC, Bloomfield Hills, MI (US)

( * ) Notice: Subject to any disclaimer, the term of this patent is extended or adjusted under 35 U.S.C. 154(b) by 1059 days.

(21) Appl. No.: 12/021,640

(22) Filed: Jan. 29, 2008

(65) Prior Publication Data

US 2008/0183045 A1 Jul. 31, 2008

Related U.S. Application Data

(60) Provisional application No. 60/887,240, filed on Jan. 30, 2007.

(51) Int. Cl.
*A61B 1/32* (2006.01)
(52) U.S. Cl. ......... 600/210; 600/206; 600/219; 600/225
(58) Field of Classification Search .................. 600/206, 600/210, 226, 219, 225
See application file for complete search history.

(56) References Cited

U.S. PATENT DOCUMENTS

| | | | |
|---|---|---|---|
| 5,728,046 A * | 3/1998 | Mayer et al. ................ | 600/210 |
| 7,014,608 B2 * | 3/2006 | Larson et al. ................ | 600/201 |
| 7,494,463 B2 * | 2/2009 | Nehls .......................... | 600/227 |
| 7,582,058 B1 * | 9/2009 | Miles et al. .................. | 600/202 |
| 7,785,253 B1 * | 8/2010 | Arambula et al. ........... | 600/219 |
| 7,955,355 B2 * | 6/2011 | Chin ............................ | 606/246 |
| 2006/0069315 A1 * | 3/2006 | Miles et al. .................. | 600/219 |
| 2006/0084844 A1 * | 4/2006 | Nehls .......................... | 600/227 |
| 2007/0106123 A1 * | 5/2007 | Gorek et al. ................. | 600/210 |
| 2009/0043311 A1 * | 2/2009 | Koros et al. ................. | 606/90 |
| 2011/0130793 A1 * | 6/2011 | Woolley et al. ............. | 606/279 |

* cited by examiner

*Primary Examiner* — Thomas C. Barrett
*Assistant Examiner* — David Bates
(74) *Attorney, Agent, or Firm* — John A. Miller; Miller IP Group, PLC

(57) ABSTRACT

A retractor device for cervical spinal fusion surgery. The retractor device includes a first post assembly having a first pin for mounting the first post assembly to a first vertebral body and a first rod coupled thereto in a multi-axial manner so that the first rod can be pivoted relative to the first pin. The retractor device also includes a second post assembly having a second pin for mounting the second post assembly to a second vertebral body and a second rod coupled thereto in a multi-axial manner so that the second rod can be pivoted relative to the second pin. The retractor device also includes a first retractor blade having a first retractor blade arm slideably engageable to the first rod, and a second retractor blade having a second retractor blade arm slideably engageable to the second rod. The first retractor blade is slid down the first rod and the second retractor blade is slid down the second rod to be positioned and separate the anatomical structures.

14 Claims, 4 Drawing Sheets

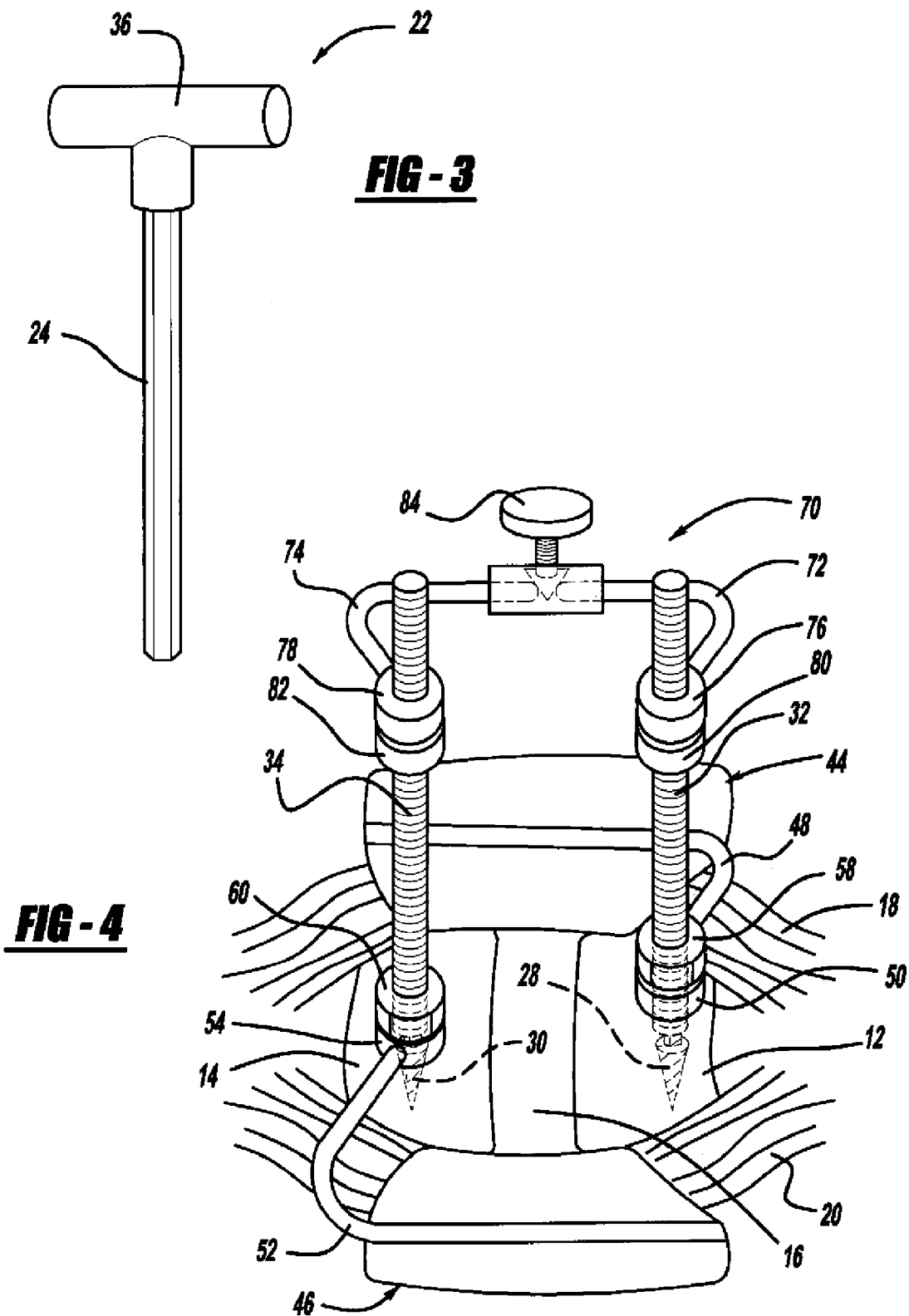

RETRACTOR DEVICE FOR CERVICAL SPINAL FUSION

CROSS-REFERENCE TO RELATED APPLICATIONS

This application claims priority to U.S. Provisional Patent Application Ser. No. 60/887,240, filed Jan. 30, 2007, titled "Retractor Device for Cervical Spinal Fusion."

BACKGROUND OF THE INVENTION

1. Field of the Invention

This invention relates to a retractor and anterior cervical plate device for anterior cervical spinal fusion and instrumentation where the device includes retractor support posts mounted to the vertebrae that provide a multi-axial orientation relative to the vertebrae to reduce retraction injury and an integrated anterior cervical plate that facilitates instrumentation placement.

2. Discussion of the Related Art

The human spine includes a series of vertebrae interconnected by connective tissue referred to as intervertebral discs that act as a cushion between the vertebrae. The discs allow for movement of the vertebrae so that the back and neck can bend and rotate.

Neck and arm pain and other related symptoms may occur when a cervical intervertebral disc herniates resulting in compression of the spinal cord and/or nerve roots. A disc herniates when some of the disc's nucleus pulposus bulges or ruptures through the annulus fibrosis. To relieve the symptoms surgeons may perform an anterior cervical discectomy to remove the offending disc material. The intervertebral space is then filled with a piece of bone or a cage filled with graft material to achieve a fusion between adjacent vertebral bodies.

To facilitate the fusion process a plate is often applied that acts to immobilize the segment and allow for bone growth between adjacent vertebral bodies. In order to perform this procedure, the surgeon makes a small incision in the front of the patient's neck to reach the cervical spine. The procedure is relatively pain free since the surgeon approaches the anterior cervical spine between natural muscle plains. The trachea and esophagus are retracted medially and the carotid artery retracted laterally to reveal the disc space.

Retraction injuries can occur since the structure must be retracted significantly for the surgeon to look straight down at the front part of the vertebrae. Additionally, significant retraction is maintained through the entire time of the procedure resulting in the vast majority of these patients waking up with significant swallowing difficulties. Up to 70% of patients undergoing anterior cervical discectomy and fusion will experience some element of swallowing difficulty after this procedure, most likely from retraction of the esophagus since the surgeon is forced to move the esophagus away from the midline. Hoarseness can also result from retraction injury to the recurrent laryngeal nerve.

In addition, the current retractor systems used require the post be inserted into adjacent vertebral bodies in order to distract open the disc space in order to perform the discectomy and place any graft material under compression. The posts are distracted and then the graft material placed into the disc space, releasing the distraction force and allowing for compression of the graft material which promotes bone fusion. The distractor posts are then removed and the anterior cervical plate is placed. Because the initial midline location of the distractor post are lost as well as their ability to expose the anterior cervical spine, the final plate placement is often crooked or off to one side of the spine. The current design takes into consideration that the distractor posts, if properly placed, mark the midline of the vertebral body and can be used to properly align and facilitate anterior cervical plate placement. This could have a detrimental effect of loading sharing forces on the plate and or intervertebral graft material resulting in graft or plate failure. Additionally, the current retractor systems often times slip out of place or rotated during the procedure which can result in injury and even perforation of the esophagus, trachea or carotid artery. It was with these limitations and potential complications associated of the currently used system that the present design was made. The currently described modifications to the anterior cervical retractor system works to reduce retractor related injury to the patient's neck structures and facilitate the surgical exposure. Additionally, the retractor system is designed to facilitate anterior plate placement.

SUMMARY OF THE INVENTION

In accordance with the teachings of the present invention, a retractor system and anterior cervical plate device for cervical spinal fusion surgery is disclosed. Both work integrally together to facilitate the operation, reduce retractor and plate placement associated complications. The retractor device includes a first post assembly having a first pin for mounting the first post assembly to a first vertebral body and a first rod coupled thereto in a multi-axial manner so that the first rod can be pivoted relative to the first pin. The retractor device also includes a second post assembly having a second pin for mounting the second post assembly to a second vertebral body and a second rod coupled thereto in a multi-axial manner so that the second rod can be pivoted relative to the second pin. The retractor device also includes a first retractor blade having a first retractor blade arm slideably engageable to the first rod, and a second retractor blade having a second retractor blade arm slideably engageable to the second rod. The first retractor blade is slid down the first rod and the second retractor blade is slid down the second rod to be positioned and separate the anatomical structures so that the surgeon can adequately view the anterior cervical spine.

Additional features of the present invention will become apparent from the following description and appended claims, taken in conjunction with the accompanying drawings.

BRIEF DESCRIPTION OF THE DRAWINGS

FIG. 3 is a perspective view of a tool for threading the post into a cervical vertebra;

FIG. 4 is a perspective view of the retractor device shown in FIG. 1 and a distractor device positioned relative to the cervical vertebrae;

DETAILED DESCRIPTION OF THE EMBODIMENTS

The following discussion of the embodiments of the invention directed to a retractor device for retracting anatomical structures during cervical spinal fusion surgery is merely exemplary in nature, and is in no way intended to limit the invention or its applications or uses. For example, the retractor device of the invention has particular application for cervical spinal fusion. However, as will be appreciated by those skilled in the art, the retractor device of the invention may have other surgical applications, including thoracic and lumbar spinal fusion.

Figures 1, 2:
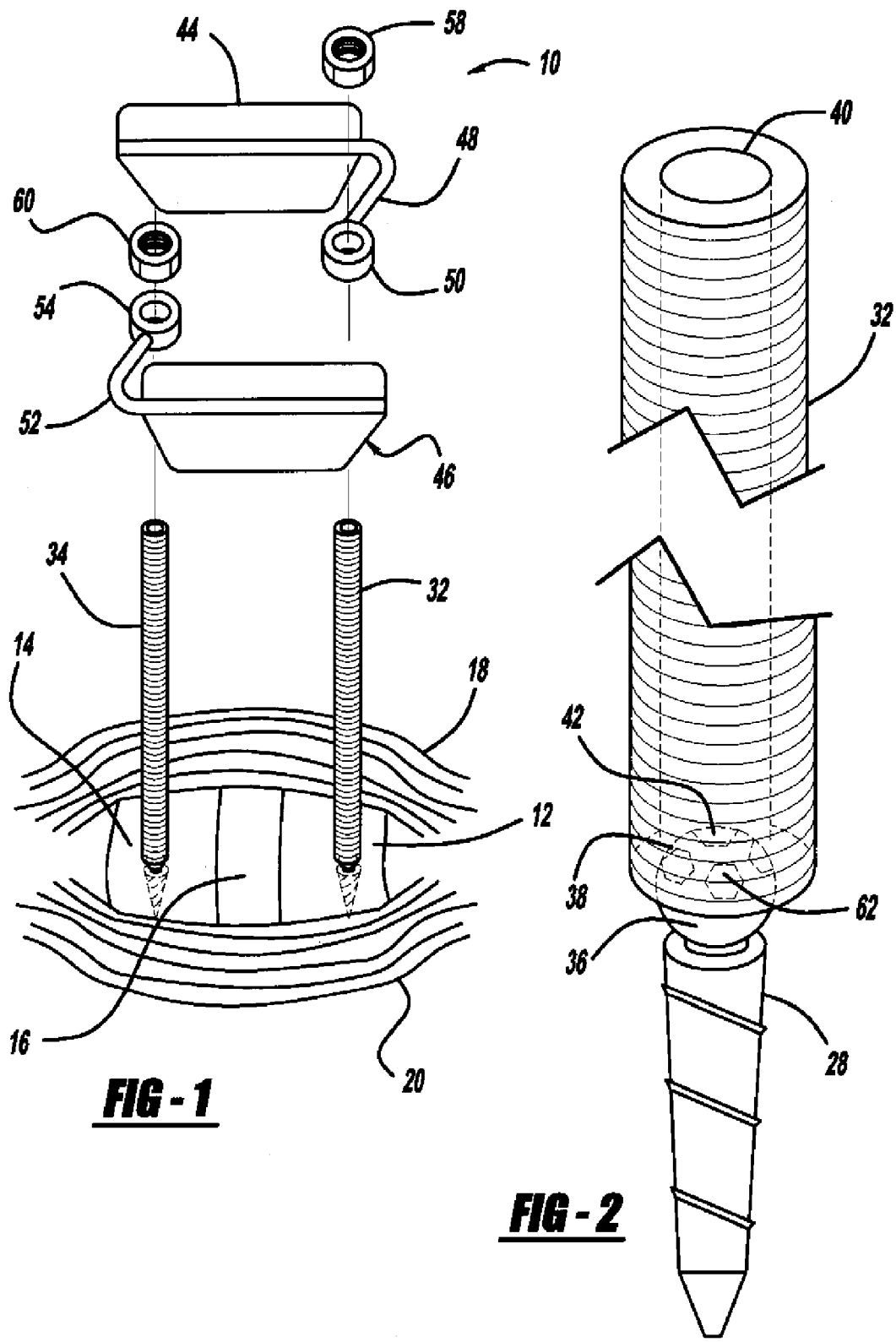
FIG. 1 is a blown-apart perspective view of a retractor device positioned relative to cervical vertebrae, according to an embodiment of the present invention.
FIG. 2 is a perspective view of a post and rod assembly in the retractor device shown in FIG. 1.

FIG. 1 is a blown-apart perspective view of a retractor device 10 employed in cervical spinal fusion procedures, such as to fuse two vertebrae 12 and 14 together after a disc 16 therebetween has been removed, according to an embodiment of the present invention. FIG. 1 shows anatomical structures 18 and 20, such as muscle, tissue, esophagus, carotid artery, trachea, etc., that may be covering or be close to the surgical area in the patient's neck. The retractor device 10 retracts or separates the anatomical structures 18 and 20 so that the surgeon is able to more easily perform the procedure. Initially, holes are drilled in the vertebral bodies of the vertebrae 12 and 14 along the midline of the spine, and retractor posts 26 and 28 are threaded into the drilled holes. Retractor rods 32 and 34 are mounted to the retractor posts 28 and 30, respectively, to allow for multi-axial orientation to help reduce retraction. The multi-axial nature of these post (as opposed to currently designed solid straight posts) allow for less retraction of the trachea and esophagus which is anticipated to reduce swallowing difficulties. The rods 32 and 34 can be mounted to the posts 26 and 28 after the posts 26 and 28 are threaded into the vertebrae 12 and 14, or the posts and rods can be part of an assembly that is mounted to the vertebrae 12 and 14.

FIG. 2 is a perspective view of the retractor post 28 and the rod 32 separated from the device 10, where the post 28 and the rod 32 are combined as an assembly, according to one non-limiting embodiment of the invention. The coupling between the post 28 and the rod 32 is multi-axial in that the rod 32 can pivot freely relative to the post 28 when the post 28 is threaded into the vertebra 12. Any suitable technique can be used to provide the multi-axial coupling between the post 28 and the rod 32. In this non-limiting embodiment, the post 28 includes a spherical head 36 mounted thereto that is inserted into a more than hemispherical opening 38 in the rod 32. Thus, the rod 32 can be pivoted relative to the post 28. In this embodiment, a bore 40 extends through the rod 32.

FIG. 3 is a perspective view of a tool 22 for threading the posts 28 and 30 into the vertebrae 12 and 14, respectively. The tool 22 includes an elongated hex-shaped body portion 24 that is inserted down the bore 40 and into an associated hex-shaped opening 42 centered at a top of the head 36. The tool 22 also includes a T-handle 36 that allows the surgeon to rotate the tool 22. Thus, the tool 22 operates as a wrench to rotate the post 28 and thread it into the drilled hole in the vertebra 12, where the post 28 can rotate independently of the rod 30.

The retractor device 10 includes a first retractor blade 44 and a second retractor blade 46. The retractor blade 44 includes an L-shaped blade arm 48 having an eyelet 50 mounted to one end. Likewise, the retractor blade 46 includes an L-shaped blade arm 52 having an eyelet 54 mounted to one end. Once the post and rod assemblies are mounted to the vertebrae 12 and 14, the blades 44 and 46 are mounted to the rods 32 and 34, respectively, by sliding the eyelets 50 and 52 down the rods 32 and 34.

FIG. 4 is a perspective view of the retractor device 10 provided in the retractor position, where the blades 44 and 46 are positioned relative to the vertebrae 12 and 14 to retract the structural anatomies 18 and 20 and expose the disc 16, as shown. The length, dimensions, size, angles, etc. of the blade arms 48 and 52 is selected so that the structural anatomies 18 and 20 are pushed a desirable distance away from the center line of the vertebrae 12 and 14. The retractor blades 44 and 46 can come in a variety of sizes and shapes. Once the retractor blades 44 and 46 are in the desired position, nuts 58 and 60 are threaded down the rods 32 and 34, respectively, and are positioned against the eyelets 50 and 54, respectively, to secure the blades 44 and 46 to the rods 32 and 34. Because the blades 44 and 46 will have a tendency to rise up, the nuts 58 and 60 will securely hold the blades 44 and 46 in place. Thus, the blades 44 and 46 are rigidly held in place, and the structural anatomies 18 and 20 are prevented from falling back into the surgical area. In an alternate embodiment, the rods 32 and 34 have a hexagonal shape and the eyelets 50 and 54 have corresponding hexagonal shape so as to lock the retractor blades 44 and 46 to the rods 32 and 34, respectively.

Because the rods 32 and 34 are pivotally mounted to the posts 28 and 30, respectively, the rods 32 and 34, and thus the retractor blades 44 and 46, can be positioned at a slightly angled orientation relative to the mid-line of the vertebrae 12 and 14. This allows the surgeon to operate from an angle "off-center" so that more sensitive structures, such as the esophagus, do not need to be pulled away from their normal position as far, thus resulting in less swallowing difficulties and discomfort to the patient after the surgical procedure. To provide this feature of the invention, the rod 32 needs to be locked at the desired angle relative to the post 28 and the rod 34 needs to be locked at the desired angle relative to the post 30. Returning to FIG. 2, the head 36 includes a plurality of hex-shaped openings 62 provided around the centerline of the head 36, as shown. A suitable tool, such as the tool 22 used to thread the post 12 into the vertebra 12, can be extended down the bore 40 and be positioned in a particular opening 62 to lock the rod 32 at the desirable angle relative to the post 28.

Once the retractor device 10 is positioned in the desired orientation, a distractor device 70 is used to separate the rods 32 and 34, and hold the vertebrae 12 and 14 apart while the disc 16 is removed from the disc space between the vertebrae 12 and 14. Typically, the injured disc 16 may be partially collapsed, where the disc height needs to be restored. The distractor device 70 holds the vertebrae 12 and 14 apart the desired distance so that bone graft material can be placed in the cleared disc space and a cervical plate can be attached to the vertebrae 12 and 14 to provide the fusion for the proper disc height.

The distractor device 70 can be any suitable distractor device for the purposes described herein. In this non-limiting embodiment, the distractor device 70 includes a first arm 72 and a second arm 74. The first arm 72 includes an eyelet 76 at an end thereof and the second arm 74 includes an eyelet 78 at an end thereof. A first nut 80 is threaded down the post 34 to the desired position and a second nut 82 is threaded down the post 32 to the desired position. The eyelet 76 is then slid down the post 34 so that it rests on the nut 80, and the eyelet 78 is slid down the post 32 so that it rests on the nut 82. A distractor knob 84 is rotated to cause the arms 72 and 74 to move apart, which causes the posts 32 and 34 to separate providing the distraction.

Figure 5:
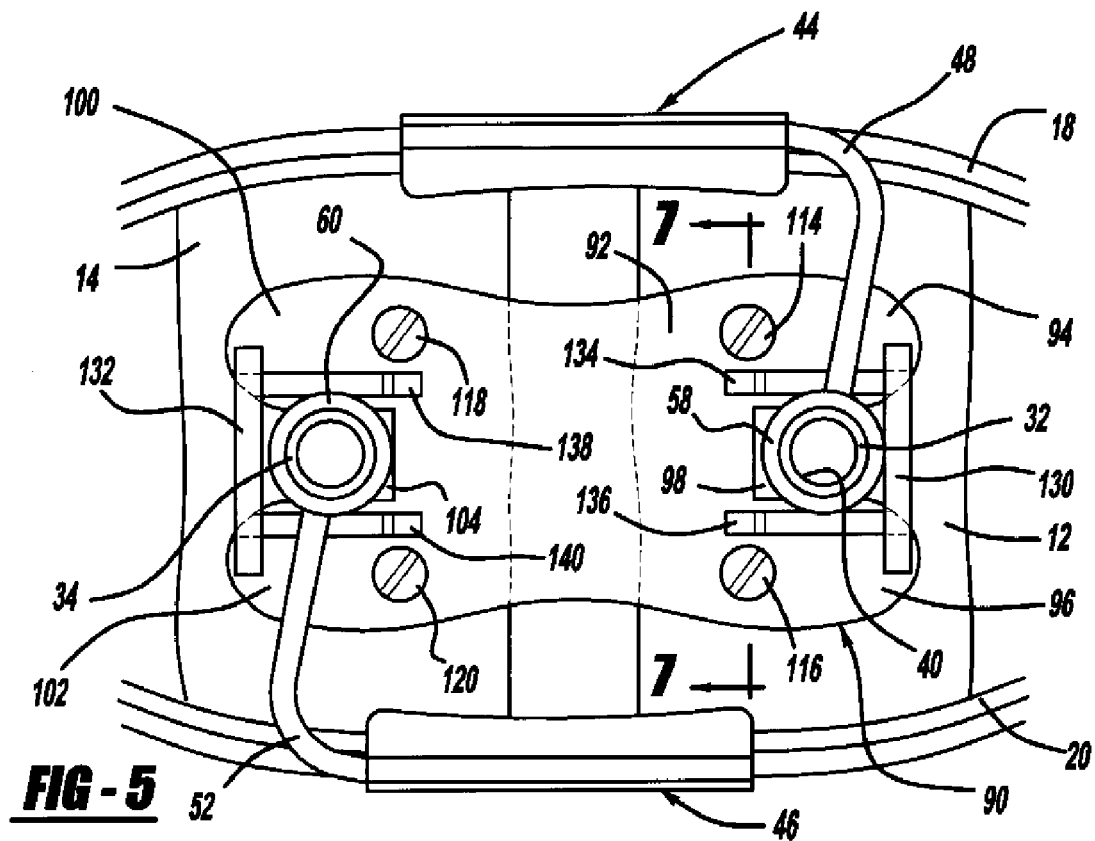
FIG. 5 is a top view of the retractor device shown in FIG. 3 and a cervical plate mounted to the vertebrae.
Figure 6:
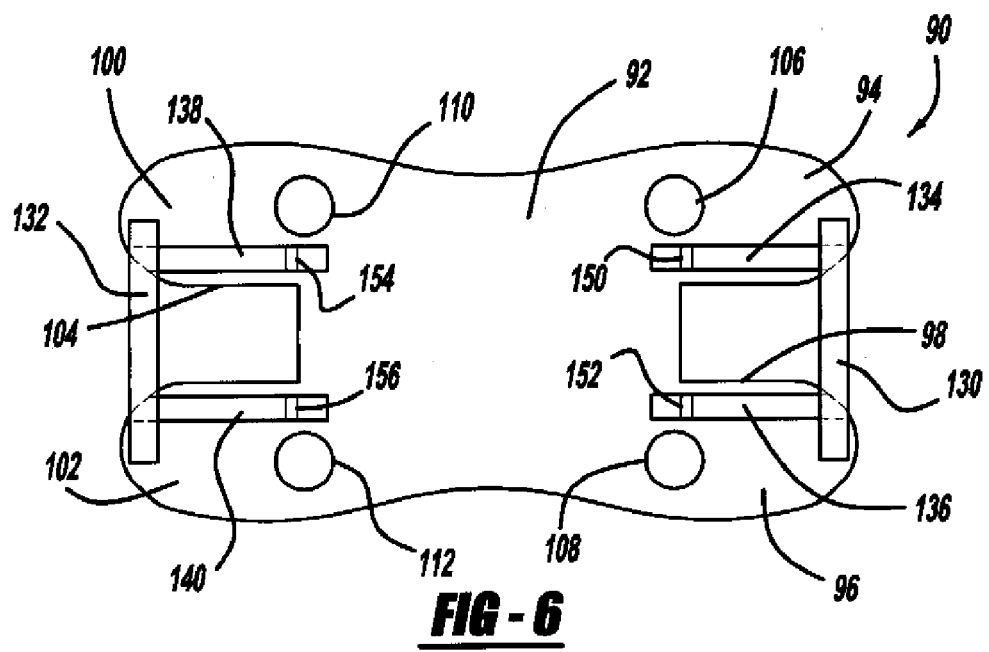
FIG. 6 is a top view of the cervical plate shown in FIG. 4 separated from the vertebrae.

Once the disc 16 has been removed and a suitable bone graft material has been positioned within the disc space, a cervical plate 90, according to the invention, is then secured to the vertebrae 12 and 14. FIG. 5 is a top view of the surgical area being discussed herein with the retractor device 10 and the cervical plate 90 in place, but with the distractor device 70 removed. FIG. 6 is a top view of the cervical plate 90 removed from the vertebrae 12 and 14. The cervical plate 90 includes a body 92 having extended portions 94 and 96 with a slot 98 therebetween at one end and extended portions 100 and 102 with a slot 104 therebetween at an opposite end. The body 92 has a general hour-glass configuration so that the bone graft material can be viewed in the disc space. When the plate 90 is attached to the vertebrae 12 and 14, the extended portions 94 and 96 are positioned on opposite sides of the rod 32 so that the rod 32 extends through the slot 98, and the extended portions 100 and 102 are positioned on opposite sides of the rod 34 so that the rod 34 extends through the slot 104.

A pair of holes 106 and 108 are provided through the body 92 proximate the extended portions 94 and 96, and a pair of holes 110 and 112 are provided through the body 92 proximate the extended portions 100 and 102, as shown. Holes (not shown) are drilled into the vertebral bodies of the vertebrae 12 and 14 that align with the holes 106, 108, 110 and 112. Suitable screws 114, 116, 118 and 120 are threaded into the drilled holes in the vertebrae 12 and 14 through the holes 106, 108, 110 and 112, respectively, in the cervical plate 90 to secure the plate 90 to the vertebrae 12 and 14 to provide the fusion. The retractor device 10 and the distractor device 70 can then be removed.

Once the screws 106, 108, 110 and 112 have been threaded into the vertebrae 12 and 14, it is generally desirable to lock the screws 106, 108, 110 and 112 in place because they have a tendency to later thread out of the vertebrae 12 and 14 as the patient moves about during normal activity. According to the invention, the plate 90 includes a locking bar 130 for locking the screws 106 and 108 in place, and a locking bar 132 for locking the screws 110 and 112 in place. The locking bar 130 slides along slots 134 and 136 and the locking bar 132 slides along slots 138 and 140.

Figure 7:
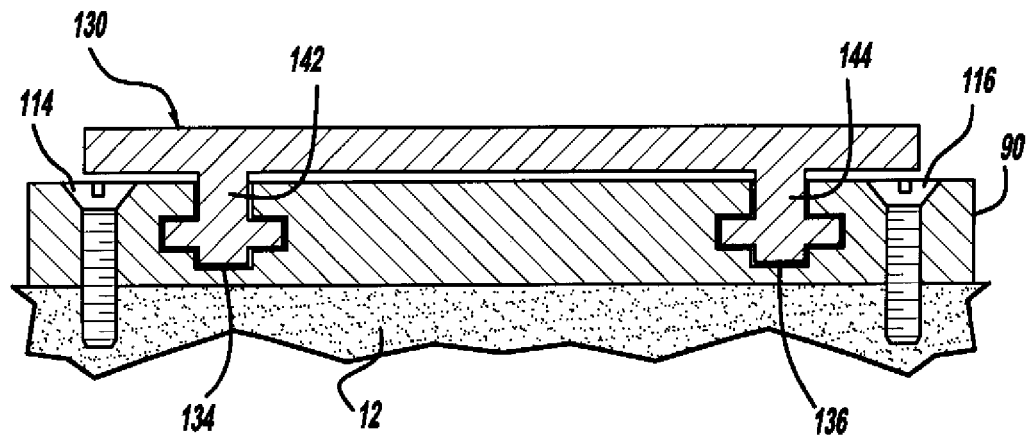
FIG. 7 is a cross-sectional view of the cervical plate mounted to the vertebrae.

FIG. 7 is a cross-sectional view through line 7-7 of the plate 90 attached to the vertebra 12 showing the locking bar 130 positioned within the slots 134 and 136, where the screws 114 and 116 are screwed into the vertebra 12 through the holes 106 and 108 in the plate 90. The locking bar 130 includes rails 142 and 144 that are positioned within the slots 134 and 136 in a secure engagement, such as shown, that allows the locking bar 130 to slide in the slots 134 and 136, but be prevented from being removed from the slots 134 and 136.

Once the screws 114 and 116 are threaded into the vertebra 12, the locking bar 130 is slid along the slots 134 and 136, so that ends of the locking bar 130 cover the screws 114 and 116, as shown, to hold them in place. A ridge 150 is provided in the slot 134 and a ridge 152 is provided in the slot 126 so that the rails 142 and 144 are forced over the ridges 150 and 152, respectively, and the locking bar 130 is snapped in place to prevent it from moving backwards in the slots 134 and 136 once it is covering the screws 114 and 116. Likewise, the slots 138 and 140 include ridges 154 and 156 to lock the locking bar 132 over the screws 110 and 112.

Figure 8:
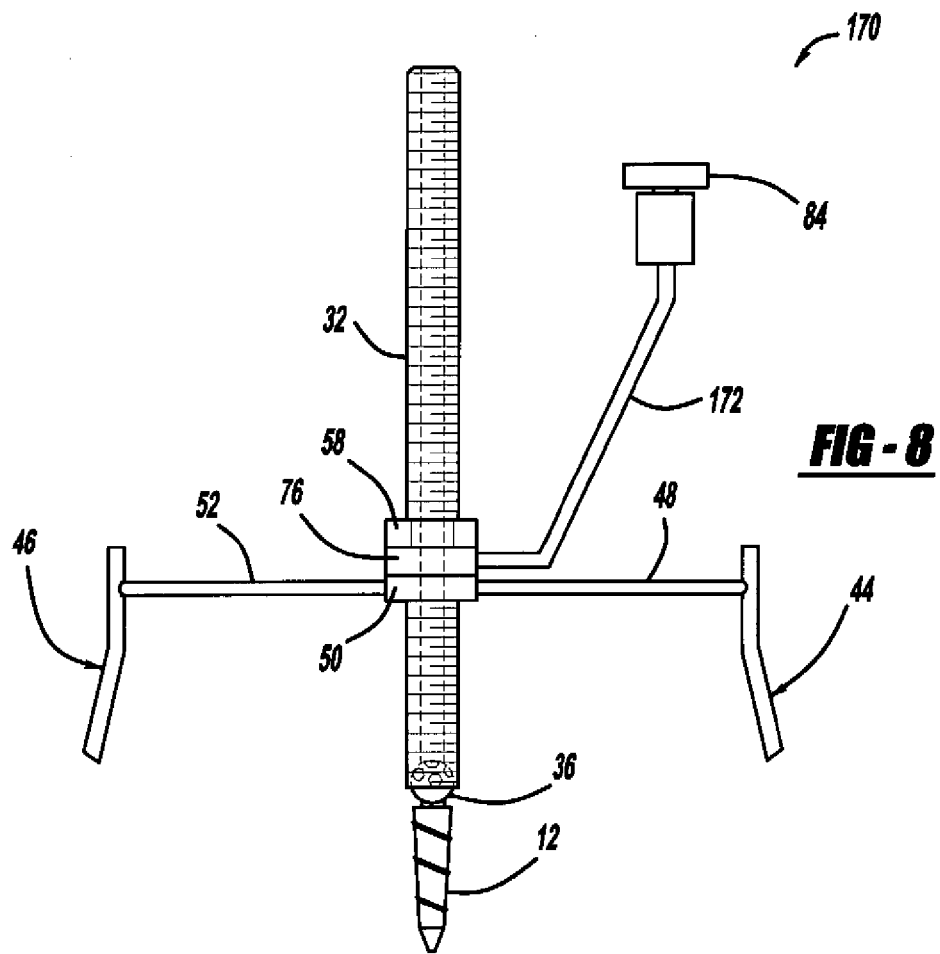
FIG. 8 is an end view of a combined retractor and distractor device, according to another embodiment of the present invention.

FIG. 8 is a side view of a combined retractor and distractor assembly 170, according to another embodiment of the present invention, where like elements described above are identified by the same reference numeral. In this embodiment, the distractor arm 72 is replaced with a distractor arm 172 that is angled up-wards, as shown. The distractor arm 74 would be replaced with a similar distractor arm coupled to the rod 34. The nuts 80 and 82 have been eliminated. The nut 58 holds both the retractor arm 48 and the distractor arm 172 in place. Likewise, the nut 60 holds both the retractor arm 52 and the other distractor arm in place.

The combination of the retractor device 10, the distractor device 70 and the cervical plate 90 offer a number of advantages over those devices known in the art. For example, the retractor device 10 is intimately associated with the vertebral distraction posts 26 and 28, unlike current systems in which they are separate. Further, the retractor blades 44 and 46 slip easily over the rods 32 and 34. The cervical plate 90 is properly positioned over the distractor posts 26 and 28. Currently, the distractor posts need to be removed and then the plate is placed.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A retractor device for retracting anatomical structures during spinal fusion surgery, said device comprising:
   a first post assembly including a first pin for mounting the first post assembly to a first vertebral body and a first rod coupled thereto, said first rod being coupled to the first pin in a multi-axial manner so that the first rod can be pivoted where the first rod is coupled to the first pin;
   a second post assembly including a second pin for mounting the second post assembly to a second vertebral body and a second rod coupled thereto, said second rod being coupled to the second pin in a multi-axial manner so that the second rod can be pivoted where the second rod is coupled to the second pin;
   a first retractor blade including a first retractor blade arm, said first retractor blade arm further including a first eyelet slideably engageable to the first rod; and
   a second retractor blade including a second retractor blade arm, said second retractor blade arm further including a second eyelet slideably engageable to the second rod, wherein the first retractor blade is slid down the first rod and the second retractor blade is slid down the second rod to be positioned and separate the anatomical structures.

2. The device according to claim 1 further comprising a first securing element for securing the first retractor blade to the first rod and a second securing element for securing the second retractor blade to the second rod.

3. The device according to claim 2 wherein the first securing element is threadably engageable to the first rod and the second securing element is threadably engageable to the second rod.

4. The device according to claim 1 wherein the first pin includes a first ball head mounted within a more than hemispherical shaped cavity in the first rod and the second pin includes a second ball head mounted within a more than hemispherical shaped cavity in the second rod to provide the multi-axial pivoting.

5. The device according to claim 4 wherein the first rod includes a bore extending therethrough and the second rod includes a bore extending therethrough, and wherein the first ball head includes an opening and the second ball head includes an opening so as to allow a tool to be inserted in the opening in the first ball head through the bore in the first rod and the opening in the second ball head through the bore in the second rod to allow the first pin to be threaded into the first vertebral body and the second pin to be threaded into the second vertebral body.

6. The device according to claim 1 further comprising a distractor assembly coupled to the first and second rods, said distractor assembly providing a distractive force separating the first and second rods.

7. The device according to claim 6 wherein the distractor assembly includes a first distractor arm including a first eyelet slideably engageable to the first rod and a second distractor arm including a second eyelet slideably engageable to the second rod.

8. A retractor device for retracting anatomical structures during spinal fusion surgery, said device comprising:
- a first post assembly including a first pin for mounting the first post assembly to a first vertebral body and a first rod coupled thereto, said first rod being coupled to the first pin in a multi-axial manner so that the first rod can be pivoted where the first rod is coupled to the first pin, said first rod including a bore extending therethrough;
- a second post assembly including a second pin for mounting the second post assembly to a second vertebral body and a second rod coupled thereto, said second rod being coupled to the second pin in a multi-axial manner so that the second rod can be pivoted where the second rod is coupled to the second pin, said second rod including a bore extending therethrough;
- a first retractor blade including a first retractor blade arm slideably coupled to the first rod; and
- a second retractor blade including a second retractor blade arm, said second retractor blade arm being slideably coupled to the second rod, where the first retractor blade is slid down the first rod and the second retractor blade is slid down the second rod to be positioned and separate the anatomical structures.

9. The device according to claim 8 wherein the first retractor blade arm includes a first eyelet slideably engageable on the first rod and the second retractor blade arm includes a second eyelet slideably engageable on the second rod.

10. The device according to claim 8 further comprising a bolt threadably engageable to the first rod to hold the first retractor blade in place and a second bolt threadably engageable to the second rod to hold the second retractor blade in place.

11. The device according to claim 8 wherein the first pin includes a first ball head mounted within a more than hemispherical shaped cavity in the first rod and the second pin includes a second ball head mounted within a more than hemispherical shaped cavity in the second rod to provide the multi-axial pivoting.

12. The device according to claim 11 wherein the first ball head includes an opening and a second ball head includes an opening so as to allow a tool to be inserted in the opening in the first ball head through the bore in the first rod and the opening in the second ball head through the bore in the second rod to allow the first pin to be threaded into the first vertebral body and the second pin to be threaded into the second vertebral body.

13. The device according to claim 8 further comprising a distractor assembly coupled to the first and second rods, said distractor assembly providing a distractive force separating the first and second rods.

14. The device according to claim 13 wherein the distractor assembly includes a first distractor arm including a first eyelet slideably engageable to the first rod and a second distractor arm including a second eyelet slideably engageable to the second rod.

* * * * *